US00PP15658P2

(12) United States Plant Patent
Richards

(10) Patent No.: US PP15,658 P2
(45) Date of Patent: Mar. 15, 2005

(54) ***VERBASCUM* PLANT NAMED 'PINK PETTICOATS'**

(50) Latin Name: *Verbascum hybrid*
Varietal Denomination: Pink Petticoats

(76) Inventor: Rodney Richards, New World Plants Ltd., Churt Road, Churt, NR. Farnham, Surrey (GB), GU10 2QS ( * ) Notice: Subject to any disclaimer, the term of this patent is extended or adjusted under 35 U.S.C. 154(b) by 36 days.

(21) Appl. No.: 10/673,972

(22) Filed: Sep. 29, 2003

(51) Int. Cl.[7] ..... A01H 5/00
(52) U.S. Cl. ..... Plt./263
(58) Field of Search ..... Plt./263, 226

*Primary Examiner*—Kent Bell

(57) ABSTRACT

*Verbascum* 'Pink Petticoats' is a new and distinct cultivar of Mullein plant with large shell pink flowers tightly clustered on racemes to 120 cm tall and effective as cut flower or for six weeks as a landscape or potted plant.

1 Drawing Sheet

Variety denomination:
Botanical classification: *Verbascum* hydrid.
Variety denomination: 'Pink Petticoats'.

BACKGROUND OF THE INVENTION

The present invention relates to the new and distinct cultivar of Mullein, botanically known as *Verbascum* hybrid (Linnaeus), and hereinafter referred to as the cultivar 'Pink Petticoats' or the "Plant". The new Plant was developed by the inventor, Rodney Richards, in 1999, at Churt, Great Britain, as a chance hybrid cross between unknown parents among several possible species and hybrids in a trial garden. It was selected in 2001 after two years of trials at a nursery in Churt, Great Britain. Mr. Richards has asexually propagated the plant by tissue culture at a nursery in Churt, Great Britain, and found the subsequent plants are identical to the original selection.

BRIEF SUMMARY OF THE PLANT

The Plant has not been observed in all possible environments. The phenotype may vary slightly with variations in growing conditions such as light intensity, day length, temperature, and water and nutrient availability without, however, any variance in genotype. The following traits have been repeatedly observed and are determined to be the unique characteristics of *Verbascum* 'Pink Petticoats':

1. Attractive, tightly clustered, ruffled, shell pink flower.
2. Tight upright branching habit of raceme.
3. Prolonged flowering season.

BRIEF DESCRIPTIONS OF THE DRAWINGS

The photographs of the new Plant demonstrate the overall appearance and unique traits of *Verbascum* 'Pink Petticoats'. Light source and direction may cause the appearance of variation in color. The colors are as accurate as reasonably possible with color reproductions.

Figure 1:
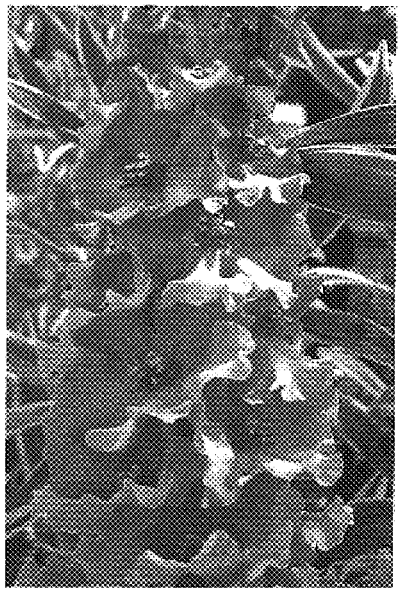

FIG. 1 — Shows a close-up of the young flowers.

Figure 2:
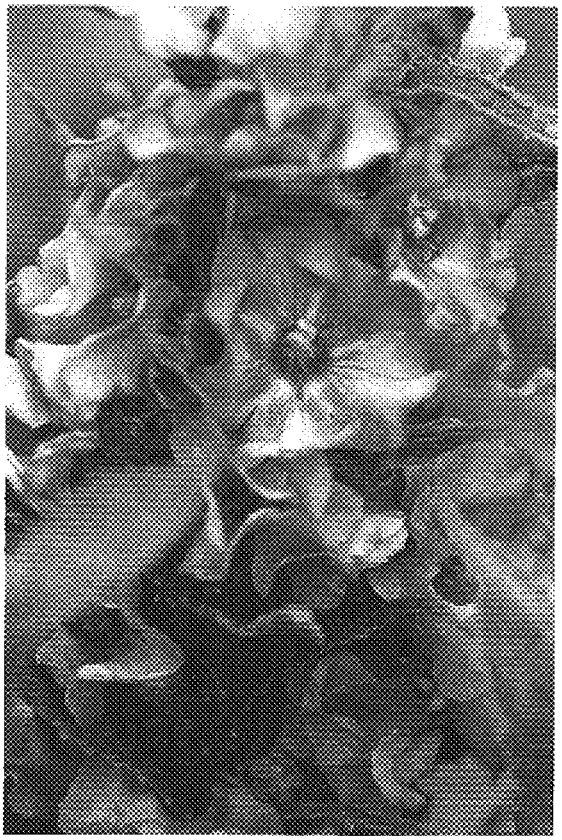

FIG. 2 — Shows a close-up of more mature flowers.

DETAILED BOTANICAL DESCRIPTION

The following description uses color references according to the 2001 edition of "The Royal Horticultural Colour Chart", except where general dictionary terms are used. The Plant described is grown in a loamy sand soil, full-sun trail gardens in Zeeland, Mich., United States of America, with fertilization and irrigation. Plants used for this observation were two years old. The Plant has not been observed in all possible environments. Some differences in phenotype have been observed where in drier gardens with higher temperatures the flower color takes on a more peachy, yellow-orange hue compared to a more pink with light purple in the center in cooler moister gardens. Such deviation does not display any genotypic differences, however.

Botanical classification: Family — Scrophulariaceae; *Verbascum* (Linnaeus) hybrid 'Pink Petticoats'.
Parentage: *Verbascum* of unknown parentage.
Propagation: Asexual by tissue culture.
Rooting time: Approximately three weeks.
Root description: Fibrous.
Plant habit and form: Basally whorled foliage with erect racemes, 40 to 48 cm tall by 50 to 60 cm across.
Growth rate: Medium to fast, finishing in a 9 cm pot in 10 to 12 weeks from cuttings.
Leaves: Acute apex; dentate margin; base without petioles, slightly cordate; 25 cm long by 8 cm wide, decreasing in size on the peduncle to 8 cm by 3 cm; coarsely denticulate; abaxial and adaxial surfaces pubescent; RHS 137 A (adaxial), RHS 137 C (abaxial).
Inflorescence: Beginning mid-June and remaining effective for six weeks.
Raceme: To 120 cm tall, considerably shorter in Great Britain, to 60 cm; 10 to 15 branches in the lower one third, un-branched above; branches to 8 mm diameter and 30 cm long, RHS 144 C.
Peduncle: 1.2 to 1.5 cm diameter; round with slight ridges; RHS 144 C.
Pedicel: 9 mm long, less than one mm diameter, near RHS N144 C.
Flowers: Perfect, usually two per node, except solitary in distal 1/10; subtended by bract; approximately 1000 to 1200 per raceme; 30 to 35 mm across, to 5 mm deep; overlapping; individual flowers lasting up to one week.
Petals: Five, undulate to sinuate, overlapping, ruffled, entire, obvate to 8 mm long and 7 mm wide in the center and narrowing to 2 mm at base; on young flowers predominantly between RHS 65 A and 65 B; on older flowers base color is RHS 186 C, petal centers and some areas RHS 186 D, RHS 19 D, and some RHS 16 D around the margin and areas that are exposed to more light.

Fragrance: None detected.

Flower buds: 5 to 7 mm diameter, 4 to 5 mm long; globose with flattened apex; RHS 185 A to RHS 185 B.

Sepals: Five, acute; 3 mm long, 2 mm wide; between RHS 143 A and 144 A on both upper and lower surfaces.

Bracts: One per flower, 8 mm long by 2 mm wide, RHS 143 A on both upper and lower surfaces.

Style: One; about 5 mm long; RHS 137 A at the stigma, gradually lightening to RHS 138 D.

Anthers: Five; about 2 mm long; adaxial side closest to RHS 59 A; filament about 4 mm, surrounded by 1 mm long fine hairs RHS 4 B in the lower ⅓.

Pollen: Saffron-colored, RHS 15 B.

Fruit: Capsule, oblong, 5 mm long, 4 mm diameter; RHS N199 B to 200 B.

Seeds: Small, rounded, less than 1 mm, dark brown.

The Plant is resistant to the same pests or diseases as other mullein, and is resistant to drought and heat, as well as cold tolerant to at least USDA Zone 5. If deadheaded after flowering 'Pink Petticoats' tends to be more perennial than other *Verbascum.*

What is claimed is:

1. I claim the new and distinct variety of the specified Mullein plant, *Verbascum* 'Pink Petticoats', essentially as herein described and illustrated, with large shell pink flowers tightly clustered on racemes to 120 cm tall and effective as cut flower or for six weeks as a landscape or potted plant.

* * * * *